US009061277B2

(12) United States Patent
Jung et al.

(10) Patent No.: US 9,061,277 B2
(45) Date of Patent: Jun. 23, 2015

(54) MICRO-FLUID SUPPLYING DEVICE HAVING GAS BUBBLE TRAPPING FUNCTION

(75) Inventors: Won-jong Jung, Seongnam-si (KR); Chin-sung Park, Yongin-si (KR); Joon-ho Kim, Seongnam-si (KR); Joon-sub Shim, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 124 days.

(21) Appl. No.: 13/298,482

(22) Filed: Nov. 17, 2011

(65) Prior Publication Data

US 2012/0309082 A1 Dec. 6, 2012

(30) Foreign Application Priority Data

Jun. 2, 2011 (KR) ........................ 10-2011-0053368

(51) Int. Cl.
*C12M 3/00* (2006.01)
*B01L 3/00* (2006.01)

(52) U.S. Cl.
CPC ........... *B01L 3/502* (2013.01); *B01L 3/502723* (2013.01); *B01L 2200/0673* (2013.01); *B01L 2200/0684* (2013.01)

(58) Field of Classification Search
CPC ......... B01L 3/50; B01L 3/502; B01L 3/5027; B01L 3/502707; B01L 3/00; B01L 2300/0816; B01L 2400/0487; B01L 3/502723; B01L 2200/0673; B01L 2200/0684
USPC ......... 422/537; 435/288.6, 288.5, 287.2, 259; 436/177
See application file for complete search history.

(56) References Cited

U.S. PATENT DOCUMENTS

| | | | | |
|---|---|---|---|---|
| 7,116,147 | B2 | 10/2006 | Kase | |
| 7,686,029 | B2 | 3/2010 | Nakao | |
| 2005/0250199 | A1* | 11/2005 | Anderson et al. | 435/287.2 |
| 2006/0205085 | A1* | 9/2006 | Handique et al. | 436/177 |
| 2007/0280857 | A1* | 12/2007 | Song et al. | 422/100 |
| 2008/0047322 | A1 | 2/2008 | Harding et al. | |

(Continued)

FOREIGN PATENT DOCUMENTS

| | | | |
|---|---|---|---|
| EP | 1855114 | A1 | 11/2007 |
| EP | 2 002 883 | A2 | 12/2008 |

(Continued)

OTHER PUBLICATIONS

Meng, D.D., et al., A Degassing Plate With Hydrophobic Bubble Capture and Distributed Venting for Microfluidic Devices, J. Micromech. Microeng. 16 (2006) pp. 419-424.*

(Continued)

*Primary Examiner* — Nathan Bowers
*Assistant Examiner* — Timothy Barlow
(74) *Attorney, Agent, or Firm* — Leydig, Voit & Mayer, Ltd.

(57) ABSTRACT

A micro-fluid supplying device having a gas bubble trapping function. The micro-fluid supplying device includes: a fluid supplier including a fluid having a biomaterial; a trap chamber in which a gas bubble is removed from the fluid supplied from the fluid supplier; and a fluid discharger which externally discharges a material supplied from the trap chamber. Material properties of a side wall and a bottom of an inside of the trap chamber are different from each other. The side wall has a better property of wetting with respect to the fluid supplied from the fluid supplier than the bottom.

13 Claims, 8 Drawing Sheets

(56) References Cited

U.S. PATENT DOCUMENTS

| | | | |
|---|---|---|---|
| 2009/0165876 | A1 | 7/2009 | Atkin et al. |
| 2010/0034704 | A1 | 2/2010 | Gu et al. |
| 2010/0218679 | A1 | 9/2010 | Hekmat et al. |

FOREIGN PATENT DOCUMENTS

| | | | |
|---|---|---|---|
| JP | 200635111 | A | 7/2004 |
| WO | WO 2004/061418 | A2 | 7/2004 |
| WO | WO 2008/114063 | A1 | 9/2008 |

OTHER PUBLICATIONS

Skelley et al., *An Active, Integrated Bubble Trap and Debubbler for Microfluidic Applications,* Twelfth International Conference on Miniaturized Systems for Chemistry and Life Sciences, Oct. 12-16, 2008, San Diego, California, USA.

Unpublished Korean Patent Application No. 10-2010-0124231, Samsung Electronics Co., Ltd. (Applicant), filed Dec. 7, 2010.

Kang et al., A Hemispherical Microfluidic Channel for the Trapping and Passive Dissipation of Microbubbles, *J.Micromech. and Microeng.,* 20: 045009 pp. 1-9 (2010).

* cited by examiner

MICRO-FLUID SUPPLYING DEVICE HAVING GAS BUBBLE TRAPPING FUNCTION

CROSS-REFERENCE TO RELATED APPLICATIONS

This application claims priority to Korean Patent Application No. 10-2011-0053368, filed on Jun. 2, 2011, and all the benefits accruing therefrom under 35 U.S.C. §119, the disclosure of which is incorporated herein in its entirety by reference.

BACKGROUND

1. Field

Provided is an apparatus related to supplying of a fluid in which an unnecessary gas is removed, and more particularly, a micro-fluid supplying device having a trapping function of a gas bubble existing as an impurity, which may be used to diagnose and analyze a bio-material.

2. Description of the Related Art

A micro-fluid supplying device processes a bio-material for analyzing and diagnosing a gene to a suitable form for analyzing and diagnosing the gene, and supplies the processed bio-material to a gene analyzing and diagnosing device. The micro-fluid supplying device includes a chamber for processing and supplying a bio-material. Such a chamber is connected to a micro-channel.

The bio-material moves through the micro-channel in a form of a liquefied sample, with another component for analyzing and diagnosing a gene. The bio-material may include a deoxyribonucleic acid ("DNA") or an enzyme.

When an unnecessary gas bubble is included in the liquefied sample, a flow of the liquefied sample through the micro-channel may be delayed or stopped, and thus a diagnosing and analyzing time of the bio-material may be increased. Also, it may be difficult to measure an accurate volume of the liquefied sample due to the gas bubble included in the liquefied sample, and thus a reaction of the liquefied sample may be stopped. Also, when the gas bubble exists in a detection zone, it may be difficult to accurately detect the bio-material.

Accordingly, an unnecessary gas bubble is removed or trapped by coating the micro-channel and a surface of the chamber, or by using a membrane or a hydrophobic film through which only a gas is selectively passes.

However, according to such a method, a gas bubble that is removed is limited, and a structure of an apparatus may be complex since a separate membrane or film is used.

SUMMARY

Provided are micro-fluid supplying devices for effectively removing an unnecessary gas bubble included in a fluid including a bio-material.

Additional aspects will be set forth in part in the description which follows and, in part, will be apparent from the description, or may be learned by practice of the presented embodiments.

Provided is a micro-fluid supplying device including: a fluid supplier including fluid including a biomaterial; a trap chamber in which a gas bubble is removed from the fluid supplied from the fluid supplier; and a fluid discharger which externally discharges a material supplied from the trap chamber. Material properties of a side wall and a bottom of the inside of the trap chamber are different from each other.

The side wall may have a better wetting property with respect to the fluid supplied from the fluid supplier than the bottom.

The fluid supplier may include: a chamber in which the bio-material is broken; a pump which pumps the broken bio-material to the trap chamber; a micro-channel which connects the bead chamber, the pump, and the trap chamber to each other, and a valve connected to the micro-channel.

The fluid discharger may include: a mixing chamber in which the material supplied from the trap chamber is mixed with a second material supplied from a unit other than the trap chamber; a pump which pumps the material supplied from the trap chamber and the second material to the mixing chamber; and a micro-channel which connects the mixing chamber, the pump, and the trap chamber to each other.

The unit which supplies the second material may be in connection with the fluid discharger. The second material may include an amplifying reagent which amplifies a certain material supplied from the trap chamber.

The unit may include a plurality of micro-channels and a plurality of pumps.

The trap chamber may include: an upper plate including a groove; and a lower plate which covers the groove. Material properties of the upper plate and the lower plate may be different from each other.

The trap chamber may include: an upper plate including a groove; a lower plate which covers the groove, and an intermediate membrane which is between the upper plate and the lower plate, and covers the groove. Material properties of the upper plate and the intermediate membrane may be different from each other. The lower plate may include a pneumatic chamber which overlaps the groove of the upper plate.

The trap chamber may include: an upper plate including a through hole; a cover layer which covers an upper side of the through hole; and a lower plate which covers a lower side of the through hole opposite to the upper side. Material properties of the cover layer and the lower plate may be the same, and the material properties of the cover layer and the lower plate may be different from a material property of the upper plate.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
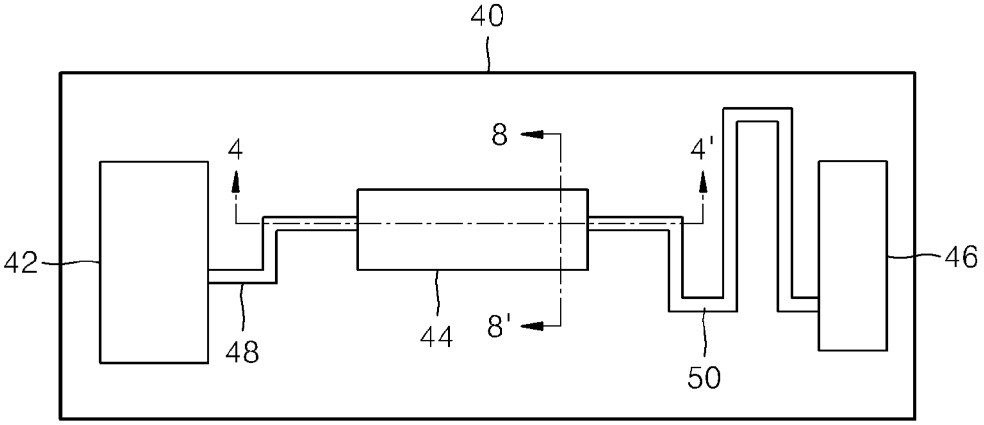
FIG. 1 is a plan view of a micro-fluid supplying device according to an embodiment of the present invention.

Reference will now be made in detail to embodiments, examples of which are illustrated in the accompanying drawings. In the drawings, like reference numerals denote like elements, and the thicknesses of layers and regions are exaggerated for clarity.

It will be understood that when an element is referred to as being "connected to" another element or layer, the element can be directly connected to another element or layer or intervening elements or layers. In contrast, when an element is referred to as being "directly connected to" another element, there are no intervening elements present. As used herein, connected may refer to elements being physically and/or fluidly connected to each other. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

FIG. 1 is a plan view of a micro-fluid supplying device 40 according to an embodiment of the present invention.

Referring to FIG. 1, the micro-fluid supplying device 40 includes a fluid supplier 42, a trap chamber 44, a fluid discharger 46, and micro-channels 48 and 50. The fluid supplier 42 supplies a fluid including an analysis sample. The analysis sample may be, for example, a bio-material or a material in which a solid state is dispersed in a liquid state. The bio-material may be a material originated from an organism. In an embodiment, for example, the bio-material may be a material including a cell or a tissue. Alternatively, the bio-material may be at least one material selected from the group consisting of a nucleic acid, protein, and a sugar. Alternatively, the bio-material may be a sample obtained from a living body, for example, at least one material selected from the group consisting of blood, urine, saliva, semen, and a biopsy sample. The solid state may be an organic particle or an inorganic particle. The inorganic particle may be polymer microbead, nanocrystal, or quantum dots.

The fluid supplier 42 may be in physical and/or fluid connection with a supplying device (not shown) which supplies a raw material. The raw material may be a cell of a certain bio-material including a nucleic acid or an enzyme. The cell of the certain bio-material may be pathogen, bacteria, virus, or fungi. The cell may be included in a suitable liquid medium. The liquid medium may be a medium for cultivating a cell, a buffer (for example, a phosphate buffered saline ("PBS") buffer), physiological saline, or water. The liquid medium may also include a cell solution.

The trap chamber 44 removes a reaction inhibition element from the fluid supplied from the fluid supplier 42. The reaction inhibition element may be a gas bubble included in the fluid. The trap chamber 44 may be a single, unitary, indivisible passage through which the fluid from the fluid supplier 42 flows. The fluid discharger 46 is a region where the fluid supplied from the trap chamber 44 is discharged to the outside of the micro-fluid supplying device 40. Another micro-device (not shown) may be in physical and/or fluid connection to the fluid discharger 46. The other micro-device may be a polymerase chain reaction ("PCR") chip. The micro-channel 48 fluidly connects the fluid supplier 42 and the trap chamber 44 to each other. Also, the micro-channel 50 fluidly connects the trap chamber 44 and the fluid discharger 46 to each other. The micro-channels 48 and 50 may include a straight portion and/or a curved portion.

Figure 2:
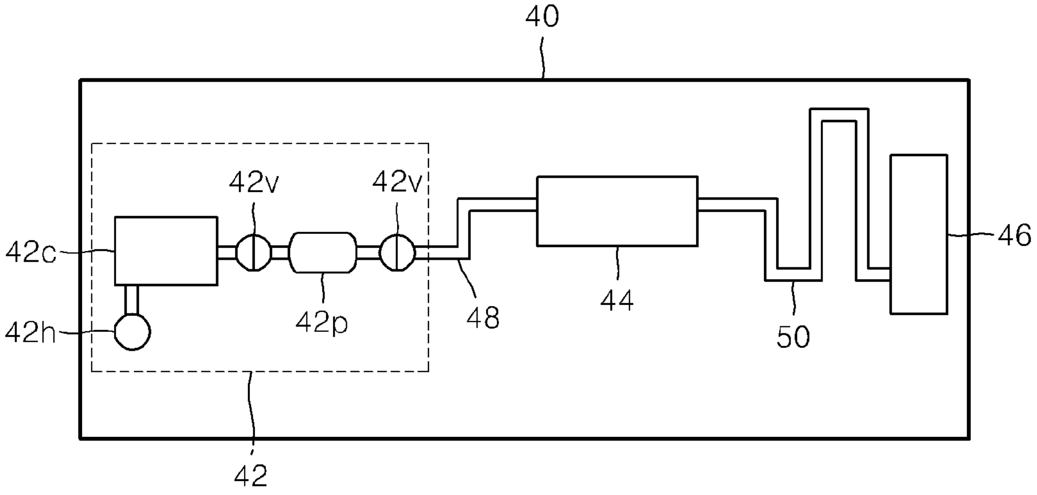
FIG. 2 is a plan view showing an example of a fluid supplier of FIG. 1.

FIG. 2 is a plan view showing an example of the fluid supplier 42 of FIG. 1.

Referring to FIG. 2, the fluid supplier 42 may include a first chamber 42*c*, a first pump 42*p*, a valve 42*v*, and micro-channels respectively fluidly connecting the first chamber 42*c*, the first pump 42*p*, and the valve 42*v* to each other. The fluid supplier 42 may include a plurality of valves 42*v*. The first chamber 42*c* may be a chamber for breaking or deforming the raw material, for example, a bead chamber. Broken or deformed raw material from the first chamber 42*c* is supplied to the trap chamber 44 by the first pump 42*p*. The first pump 42*p* may be a motor operated valve ("MOV") pump. The first chamber 42*c* and the first pump 42*p* are fluidly connected through a first micro-channel therebetween, and a first valve 42*v* is connected to the first micro-channel. The fluid flowing through the first micro-channel is controlled by the first valve 42*v*. The first pump 42*p* and the trap chamber 44 are also fluidly connected through a second micro-channel therebetween. A second valve 42*v* is also connected to the second micro-channel.

The fluid supplier 42 includes a hole 42*h*. The raw material may be supplied from the outside of the fluid supplier 42 to the first chamber 42*c* of the fluid supplier 42 through the hole 42*h*. The hole 42*h* and the first chamber 42*c* are connected through a third micro-channel, and a valve (not shown) may be connected to the third micro-channel. The fluid supplier 42 may further include at least one hole (not shown), aside from the hole 42*h*. A material used to break the raw material may be supplied through the at least one hole. The at least one hole and the first chamber 42*c* are connected through a micro-channel (not shown), and a valve (not shown) is connected to the micro-channel. The valves that are not shown may be identical to the valve 42*v* connected to the micro-channel between the first chamber 42*c* and the first pump 42*p*.

Figure 3:
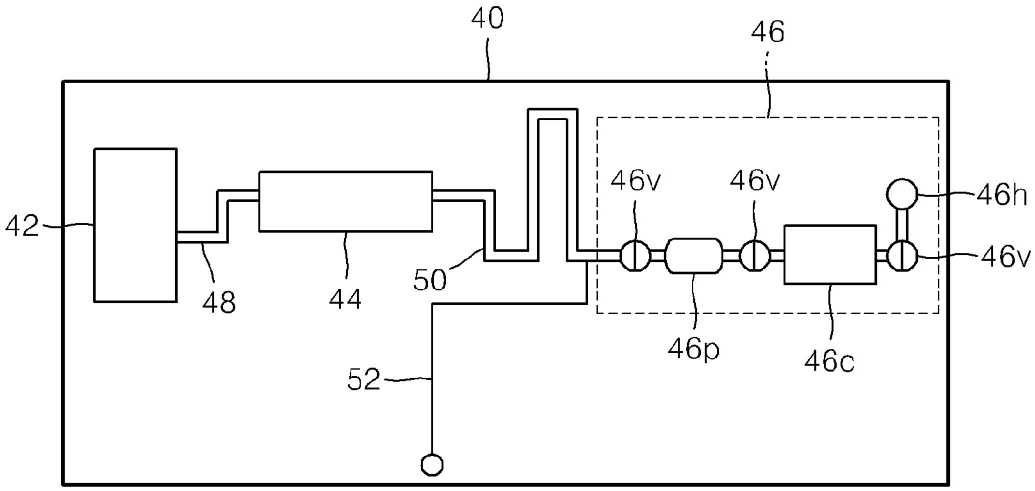
FIG. 3 is a plan view showing an example of a fluid discharger of FIG. 1.

FIG. 3 is a plan view showing an example of the fluid discharger 46 of FIG. 1.

Referring to FIG. 3, the fluid discharger 46 may include a second pump 46*p*, a second chamber 46*c*, a valve 46*v*, and micro-channels respectively connecting the second pump 46*p*, the second chamber 46*c*, and the valve 46*v* to each other. The fluid discharger 46 may include a plurality of valves 46*v*. The second pump 46*p* supplies a fluid discharged from the trap chamber 44 to the second chamber 46*c*. A third valve 46*v* is connected to the micro-channel 50 between the second pump 46*p* and the trap chamber 44. The third valve 46*v* between the second pump 46*p* and the trap chamber 44 may be connected closer to the second pump 46*p*.

The second chamber 46c mixes at least two materials transmitted to the second chamber 46*c*. The at least two materials may include at least a material from broken or deformed cells and an amplifying reagent. The remaining of the at least two materials may be supplied through another micro-channel 52 in fluid connection to the micro-channel 50 between the third valve 46*v* in front of the second pump 46*p* and the trap chamber 44. The another micro-channel 52 may include a plurality of micro-subchannels, and a pump and a valve may be connected to some of the plurality of the micro-subchannels.

The at least two materials mixed in the second chamber 46*c* are discharged to an external device connected to the fluid discharger 46. The external material may be a bio-material detecting and analyzing device, such as a PCR chip.

A fourth valve 46*v* for controlling a flow of the fluid is connected to a fourth micro-channel between the second pump 46*p* and the second chamber 46*c*. The fluid discharger 46 includes a hole 46*h*. A result product obtained by mixing the at least two materials in the second chamber 46*c* is supplied to the external device through the hole 46*h*. The hole 46*h* and the second chamber 46*c* are fluidly connected to each other by a fifth micro-channel, and a fifth valve 46*c* is in physical and fluid connection with the fifth micro-channel. The valves 46*v* may be identical to the valves 42*v* included in the fluid supplier 42 of FIG. 2.

FIGS. 4 through 7 are cross-sectional views taken along a line 4-4' of a region including the trap chamber 44 of FIG. 1, according to embodiments of the present invention.

Figure 4:
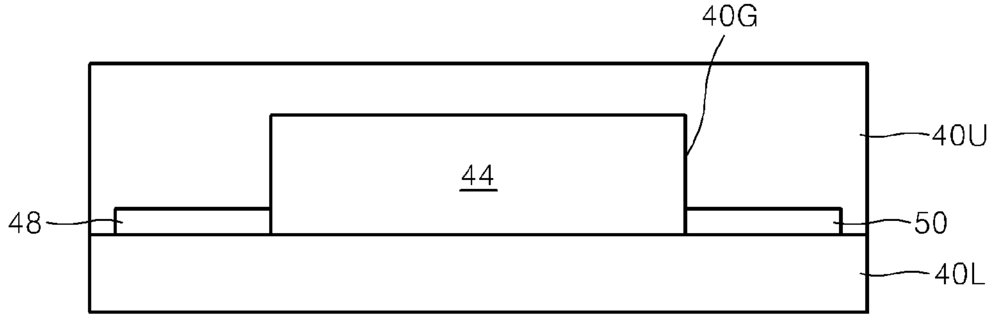
FIG. 4 is a cross-sectional view taken along a line 4-4' of a region including a trap chamber of FIG. 1, according to an embodiment of the present invention.

Referring to FIG. 4, the micro-fluid supplying device 40 includes a lower plate 40L and an upper plate 40U. The lower plate 40L may be a flexible substrate or an inflexible substrate. An upper surface of the lower plate 40L constituting a bottom surface of the trap chamber 44 may have a worse wetting property with respect to the fluid supplied from the fluid suppler 42 than a side of a groove 40G of the upper plate 40U. When the lower plate 40L is a flexible substrate, the lower plate 40L may be a polymer membrane having elasticity. In an embodiment, for example, the lower plate 40L may include silicon rubber, polydimethylsiloxane ("PDMS"), or any flexible material aside from PDMS. The lower plate 40L may be a membrane having liquid non-penetrability or porosity. When the lower plate 40L is a membrane having porosity, a pore size of the membrane may be smaller than a size of a target material to be analyzed. In one embodiment, for example, the membrane may not pass a bio-polymer, such as deoxyribonucleic acid ("DNA"), protein, or polysaccharide, therethrough, but may pass a reaction inhibition element, such as a gas bubble, which deteriorates diagnosing and analyzing the bio-material, therethrough. When the lower plate 40L is an inflexible substrate, the lower plate 40L may be a metal substrate.

The upper plate 40U includes the groove 40G. The groove 40G extends into an interior of the upper plate 40U from one surface of the upper plate 40U facing the upper surface of the lower plate 40L. The groove 40G of the upper plate 40U is covered (e.g., completely overlapped) by the lower plate 40L. The groove 40G covered by the lower plate 40L defines the trap chamber 44. The upper plate 40U includes the micro-channels 48 and 50. The micro-channels 48 and 50 are grooves which extend from the surface of the upper plate 40U, e.g., the surface of the upper plate 40U facing the lower plate 40L. However, depths of the micro-channels 48 and 50 are smaller than a depth of the groove 40G used as the trap chamber 44. The depths are taken perpendicular to the surface of the upper plate 40U. One of the micro-channels 48 and 50 may be a fluid inflow channel of the trap chamber 44, and the other may be a fluid discharge channel of the trap chamber 44. One of the micro-channels 48 and 50 is in physical and/or fluid connection with the groove 40G at one side of the groove 40G, and the other is in physical and/or fluid connection to another side of the groove 40G such as an opposing side. The micro-channels 48 and 50 are also covered (e.g., completely overlapped) by the lower plate 40L. The micro-channels 48 and 50 covered by the lower plate 40L define fluid passages. Accordingly, the micro-channels 48 and 50 may be used as passages for a liquefied fluid. The upper plate 40U of the trap chamber 44 may be a glass substrate or a polymer substrate. A wetting property of an inner surface of the groove 40G with respect to a fluid flowing into the trap chamber 44 is better than that of the upper surface of the lower plate 40L.

Figure 5:
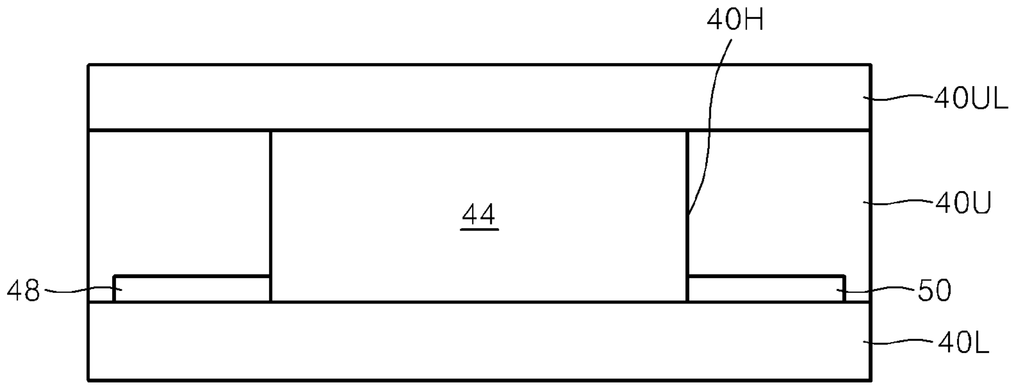
FIG. 5 is a cross-sectional view showing an example including a through hole instead of a groove in FIG. 4.

Instead of the groove 40G, the upper plate 40U may include a through hole 40H as shown in FIG. 5. Also, a cover layer 40UL for covering (e.g., overlapping an entire of) the through hole 40H may be disposed on the upper plate 40U. Since the top and bottom of the through hole 40H are respectively covered by the cover layer 40UL and the lower plate 40L, the through hole 40H may be used as the trap chamber 44.

The cover layer 40UL may be a flexible or inflexible layer. When the cover layer 40UL is a flexible layer, the cover layer 40UL may include PDMS. A property of a surface of the cover layer 40UL covering the through hole 40H may be different from a property of the upper plate 40U. In one embodiment, for example, a wetting property of the cover layer 40UL with respect to the fluid supplied from the fluid supplier 42 may be worse than an inner surface of the groove 40G of the upper plate 40U. In other words, the cover layer 40UL may include a material having a worse wetting property with respect to the fluid supplied from the fluid supplier 42 than the inner surface of the groove 40G. The cover layer 40UL may have the same or similar property as the lower plate 40L described above. A gas trapped in the trap chamber 44 of FIG. 5 may be discharged through the cover layer 40UL. Here, the gas may be forcibly discharged by using an external pump.

Figure 6:
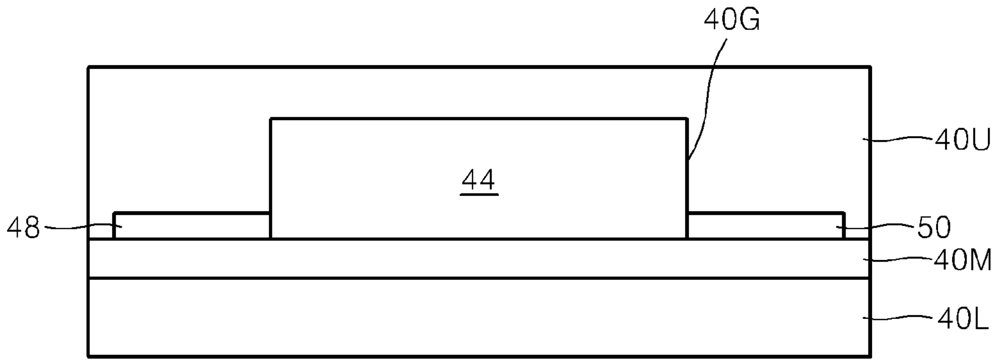
FIG. 6 is a cross-sectional view showing an example including an intermediate membrane between a lower plate and an upper plate in FIG. 4.

According to another embodiment of the present invention, an intermediate membrane 40M may be further disposed between the lower plate 40L and the upper plate 40U as shown in FIG. 6. The intermediate membrane 40M may be a thin flexible membrane. The intermediate membrane 40M may have the same material penetrating property as the lower plate 40L described with reference to FIG. 4. Accordingly, the lower plate 40L of FIG. 6 may be a substrate without flexibility. In FIG. 6, the bottom of the trap chamber 44 is an upper surface of the intermediate membrane 40M. Also, the micro-channels 48 and 50 are covered by the intermediate membrane 40M. The upper surface of the intermediate membrane 40M in the trap chamber 44 may have a lower wetting property than the upper plate 40U with respect to the fluid flowing into the trap chamber 44. The intermediate membrane 40M of FIG. 6 may be identically applied to FIG. 5, and such application is obvious from FIGS. 5 and 6, and thus descriptions thereof will be omitted herein.

Figure 7:
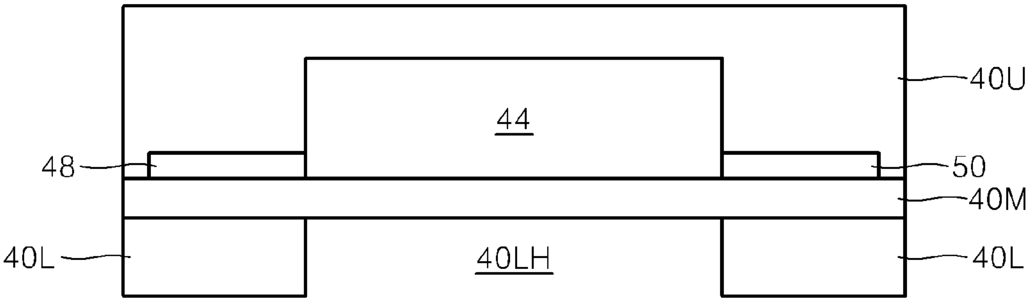
FIG. 7 is a cross-sectional view of a modified example of FIG. 6.

The lower plate 40L of FIG. 6 may include a through hole 40LH as shown in FIG. 7. Referring to FIG. 7, the through hole 40LH is disposed below the trap chamber 44. The through hole 40LH and the trap chamber 44 are separated from each other by the intermediate membrane 40M. In FIG. 7, the intermediate membrane 40M is non-penetratable to the bio-material but penetratable to a gas. Accordingly, a gas trapped in the trap chamber 44 may be discharged through the through hole 40LH. Thus, the through hole 40LH of the lower plate 40 may be a pneumatic chamber. A pump may be used to discharge the gas through the through hole 40LH. When the gas trapped in the trap chamber 44 is externally dischargeable as in FIGS. 5 and 7, the volume of a fluid including a gas bubble, which flows into the trap chamber 44, may be larger than the volume of the trap chamber 44.

Figure 8:
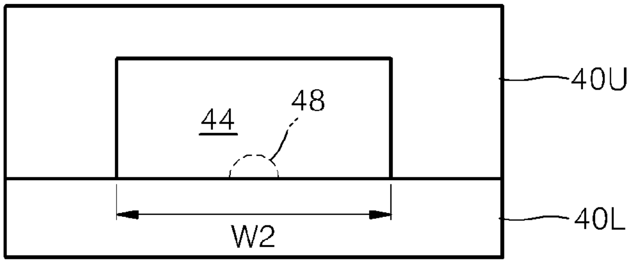
FIG. 8 is a cross-sectional view taken along a line 8-8' of a region including the trap chamber of FIG. 1, according to an embodiment of the present invention.

FIG. 8 is a cross-sectional view taken along line 8-8' of a region including the trap chamber 44 of FIG. 1, according to an embodiment of the present invention.

Referring to FIG. 8, the upper plate 40U is disposed on the lower plate 40L, and the trap chamber 44 is formed by combining the lower plate 40L and the upper plate 40U. A vertical width W2 of the trap chamber 44, e.g., a width in a direction of the line 8-8' of FIG. 1 perpendicular to a flow direction in the trap chamber 44, may be smaller than, identical to, or larger than a horizontal width (e.g., a width in a direction of line 4-4' of FIG. 1 in the flow direction) of the trap chamber 44.

Figure 9:
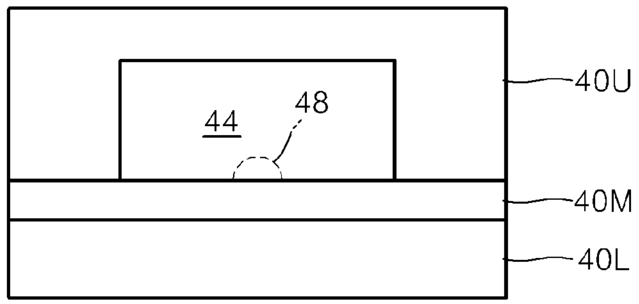
FIG. 9 is a cross-sectional view showing a case when an intermediate membrane is disposed between a lower plate and an upper plate of FIG. 8.

FIG. 9 is a cross-sectional view showing a case when the intermediate membrane 40M is disposed between the lower plate 40L and the upper plate 40U of FIG. 8. A composition of FIG. 9 is identical to that of FIG. 6, except a direction of a cross-section. As described with reference to FIG. 5, the trap chambers 44 of FIGS. 8 and 9 may be the through hole 40H penetrating through the upper plate 40U.

Figure 10:
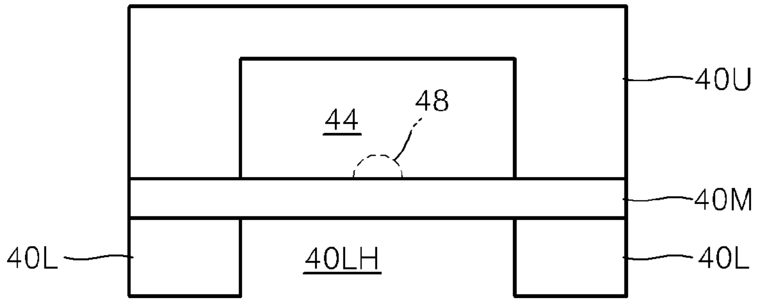
FIG. 10 is a cross-sectional view of a modified example of FIG. 9.

The lower plate 40L of FIG. 9 may include a through hole 40LH as shown in FIG. 10.

Although the widths of the bottom and the top of the trap chamber 44 are the same in FIGS. 4 through 10, the widths may be different. In an alternative embodiment, for example, the width of the top may be wider than the width of the bottom of the trap chamber 44.

Figure 11:
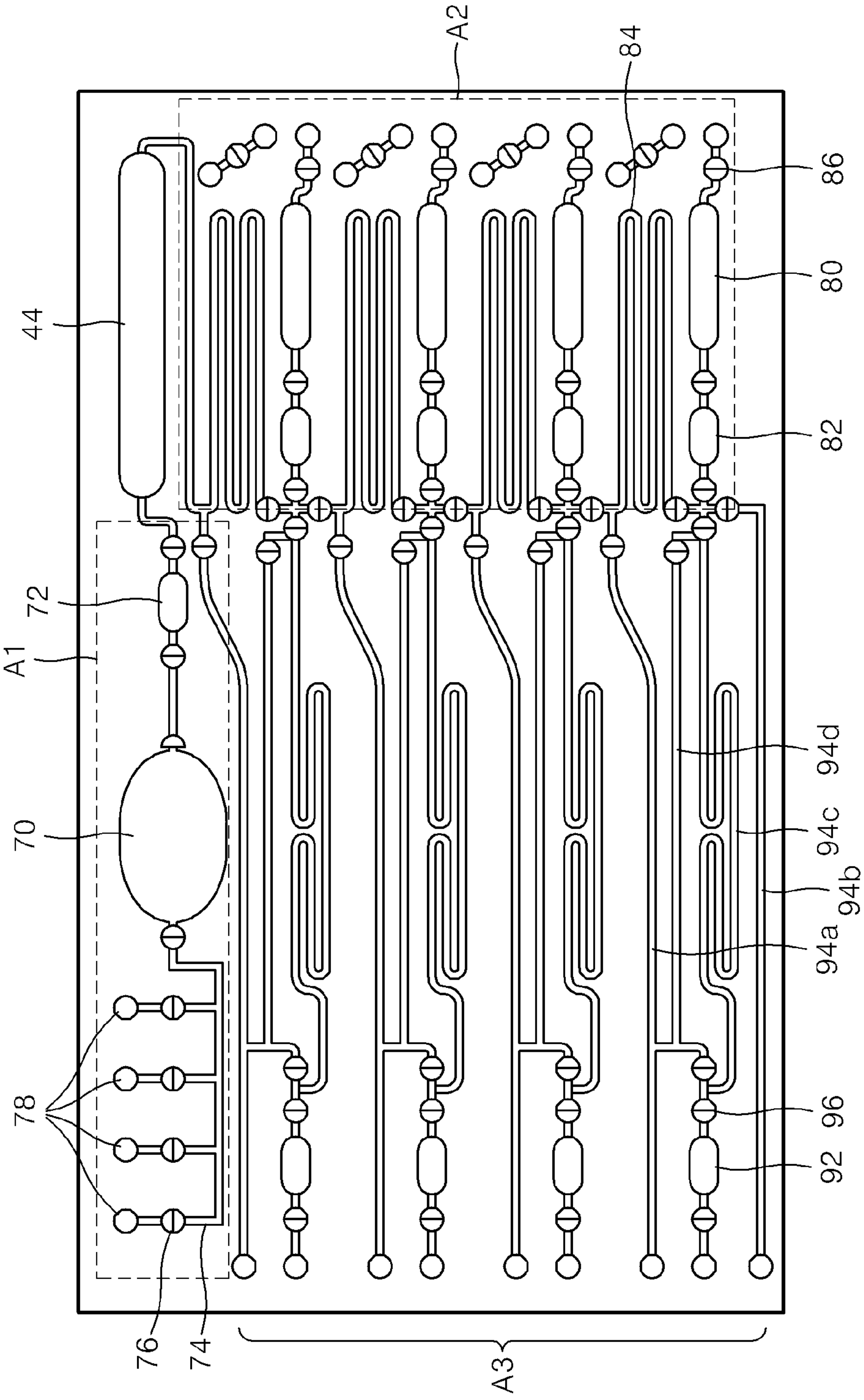
FIG. 11 is a plan view of the micro-fluid supplying device of FIG. 1 including a trap chamber, according to an embodiment of the present invention.

FIG. 11 is a plan view of the micro-fluid supplying device of FIG. 1 including the trap chamber 44 described above, according to an embodiment of the present invention.

In FIG. 11, a first area A1 may be an example of the fluid supplier 42 of FIG. 1. Also, a second area A2 may be an example of the fluid discharger 46 of FIG. 1. Also, a third area A3 may be an example of an area including the micro-channel 52 described with reference to FIG. 3. The first and second areas A1 and A2 are connected to each other by the trap chamber 44.

The first area A1 includes a bead chamber 70 and a pump 72, the bead chamber 70 and the pump 72 are physically and/or fluidly connected by a micro-channel 74, and valves 76 are connected to the micro-channel 74. A cell for examination, dry air, a cell solution, a wash, etc., may flow into the bead chamber 70 through holes 78 connected to the micro-channel 74. Here, the cell for examination may be transmitted with a solution including the cell for examination.

The second area A2 includes a mixing chamber 80 and a pump 82, the mixing chamber 80 and the pump 82 are physically and/or fluidly connected by a micro-channel therebetween, and a pump 86 is connected to the micro-channel. The mixing chamber 80 is connected to a discharging end of the pump 82, and a micro-channel 84 having a predetermined length is connected to an inflow end of the pump 82. One mixing chamber 80, one pump 82, and one micro-channel 84 may form a fluid discharging unit set. The second area A2 includes a plurality of such fluid discharging unit sets. The fluid discharging unit sets are connected in parallel.

The third area A3 includes a plurality of pumps 92, micro-channels 94*a* through 94*d*, and a plurality of valves 96. The micro-channels 94*a* through 94*d* of the third area A3 may correspond to the other micro-channel 52 of FIG. 3. One pump 92 and the micro-channels 94*a* through 94*d* may form a unit set. The third area A3 includes a plurality of such unit sets that are disposed in parallel. The unit sets in the third area A3 are respectively connected to the fluid discharging unit sets in the second area A2. The third area A3 may be a second supplier that supplies a second supplied material, which is different from a supplied material supplied from the first area A1, to the second area A2. The second supplied material may be at least an amplifying reagent. For detailed descriptions about the first through third areas A1 through A3, refer to Korean Patent Application No. 2010-124231 (Apparatus for analyzing gene and method of analyzing gene by using the apparatus).

A process of removing a gas bubble from the trap chamber 44 will now be described with reference to FIG. 12.

Figure 12:
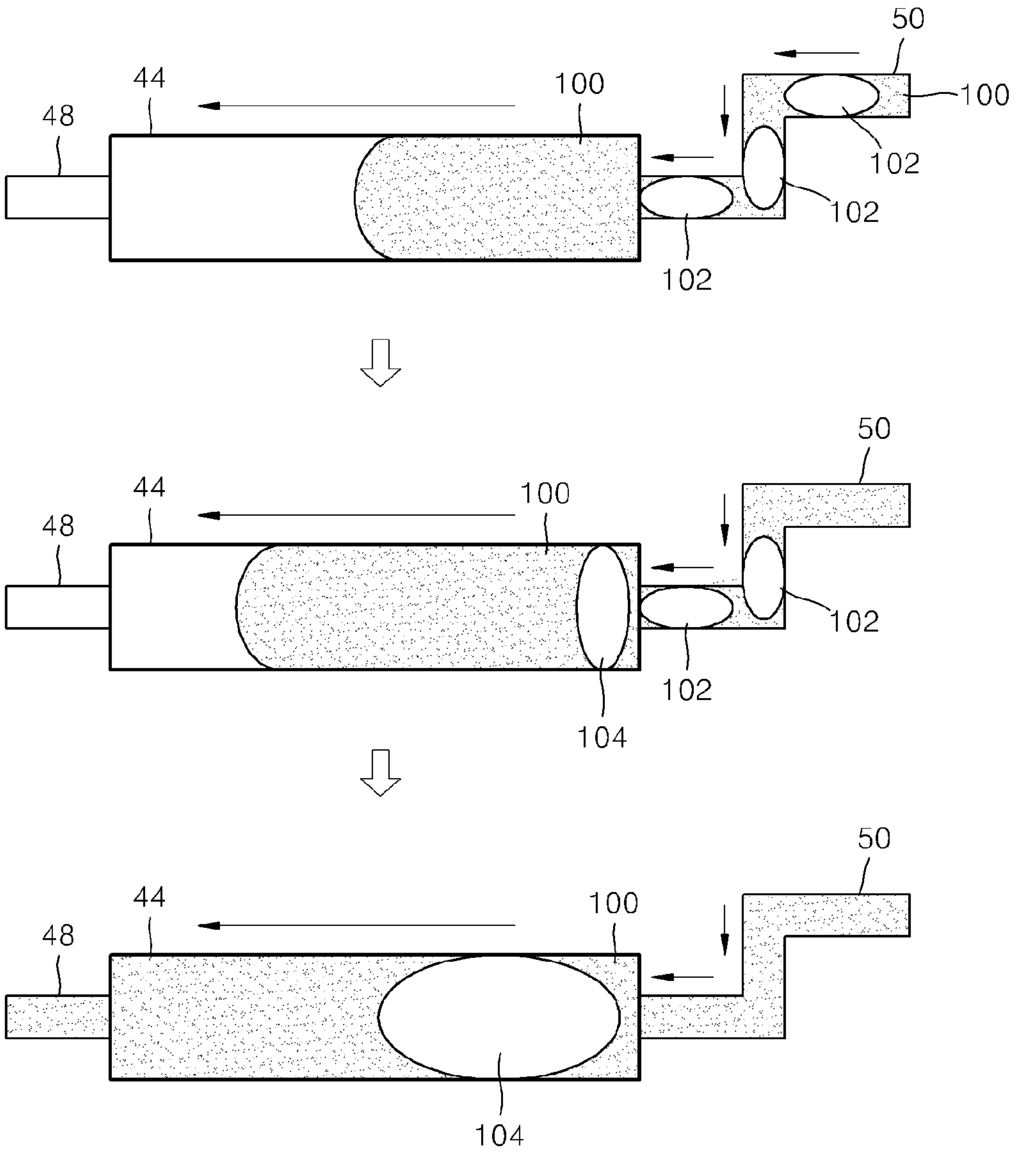
FIG. 12 is a plan view describing a process of removing a gas bubble from a trap chamber.

FIG. 12 is a plan view describing a process of removing a gas bubble from the trap chamber 44.

For convenience, FIG. 12 only illustrates the plan view of the trap chamber 44, and the micro-channels 48 and 50 respectively connected to the ends of the trap chamber 44.

Referring to the top and middle illustrations in FIG. 12, when a fluid 100 including a gas bubble 102 flows into the trap chamber 44 through the micro-channel 50, a gas bubble that first flows into and is trapped in the trap chamber 44 operates as a bubble seed for gathering following gas bubbles. The following gas bubbles 102 gather around the bubble seed that first entered the trap chamber 44 and was trapped. The fluid 100 moves in a direction indicated by arrows in the trap chamber 44, and here, a side of the inside of the trap chamber 44 may have a better wetting property with respect to the fluid 100 than the bottom of the trap chamber 44. Thus, the fluid 100 moves faster along the side of the inside of the trap chamber 44.

Referring to the middle and bottom illustrations in FIG. 12, accordingly, the fluid 100 behind a trapped gas bubble 104 moves to the front of the trapped gas bubble 104 along the side of the trap chamber 44, and the gas bubble 102 flowing into the trap chamber 44 is combined to the trapped gas bubble 104. As such, in the fluid 100 flowing into the trap chamber 44 through the micro-channel 50, a liquefied portion moves toward the left in the plan view of the trap chamber 44, and the gas bubbles 102 in the fluid 100 gather as the trapped gas bubble 104 at the right in the trap chamber 44 based on FIG. 12. The fluid 100 moving to the left in the trap chamber 44 does not include a gas bubble. As a result, the fluid 100 which has entered into the trap chamber 44 is completely divided into the liquefied (e.g., non-gas) portion and a gas portion. When a fluid that does not include a gas bubble is used, e.g., when the fluid is a bio-material for diagnosing a gene including a nucleic acid, the gene may be quickly and accurately analyzed and diagnosed. Also, when the fluid not including a gas bubble is a reaction material for a certain reaction, the certain reaction may be continuously generated and reaction efficiency may be increased.

Figure 13:
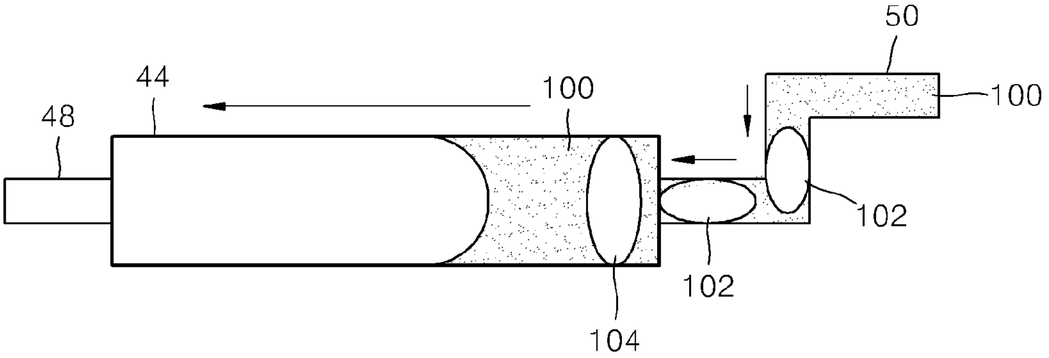
FIG. 13 is a plan view showing a case when a front portion of a fluid from which a gas bubble is removed is concave, while removing a gas bubble from a trap chamber.

If the side of the inside of the trap chamber 44 is not dry and instead is wet, a front portion of the fluid 100 from which the gas bubbles 102 and 104 are removed is not convex, but concave as shown in FIG. 13, inside the trap chamber 44. As such, a contacting area of the trap chamber 44 and the fluid 100 increases.

As described above, an unnecessary gas bubble can be effectively removed from a fluid including a bio-material by using a micro-fluid supplying device according to an embodiment of the present invention, since a difference of properties inside a trap chamber, e.g., a difference of wetting degrees, is used. Accordingly, by using the bio-material supplied from the micro-fluid supplying device, stopping of a reaction of the bio-material can be reduced or effectively prevented due to the unnecessary gas bubble, thereby increasing reliability of a reaction result. Also, the fluid including the bio-material can smoothly flow in an apparatus for diagnosing and analyzing the bio-material, and a volume of the fluid can be accurately measured. Further, since a separate membrane or film is not used, a removable gas bubble is not limited, and a structure of the micro-fluid supplying device is not complex.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A micro-fluid supplying device comprising:

a fluid supplier that supplies a fluid including a bio-material;

a trap chamber which is in connection with the fluid supplier and in which a gas bubble is removed from the fluid supplied from the fluid supplier;

a fluid discharger which is in connection with the trap chamber and externally discharges a material supplied from the trap chamber;

an upper plate comprising a groove defining side walls of the trap chamber;

an intermediate membrane covering the groove; and a lower plate;

wherein the intermediate membrane is between the upper plate and the lower plate, and an upper surface of the intermediate membrane is the bottom surface of the trap chamber, wherein a sidewall of the groove has a better wetting property with respect to the fluid supplied from the fluid supplier than the intermediate membrane;

and wherein the lower plate is separated from the trap chamber by the intermediate membrane.

2. The micro-fluid supplying device of claim 1, wherein the fluid supplier comprises:

a chamber in which the bio-material is ruptured;

a pump which pumps the ruptured bio-material to the trap chamber;

a micro-channel which connects the chamber in which the biomaterial is ruptured, the pump, and the trap chamber to each other; and a valve in connection with the micro-channel.

3. The micro-fluid supplying device of claim 1, wherein the fluid discharger comprises:

a mixing chamber in which the material supplied from the trap chamber is mixed with a second material supplied from a unit other than the trap chamber;

a pump which pumps the material supplied from the trap chamber and the second material to the mixing chamber; and a micro-channel which connects the mixing chamber, the pump, and the trap chamber to each other.

4. The micro-fluid supplying device of claim 3, wherein the unit which supplies the second material is in connection with the fluid discharger.

5. The micro-fluid supplying device of claim 3, wherein the second material comprises an amplifying reagent which amplifies a certain material supplied from the trap chamber.

6. The micro-fluid supplying device of claim 4, wherein the unit that supplies the second material comprises a plurality of micro-channels and a plurality of pumps.

7. The micro-fluid supplying device of claim 1, wherein the lower plate comprises a pneumatic chamber which overlaps the groove of the upper plate and is separated from the trap chamber by the intermediate membrane.

8. The micro-fluid supplying device of claim 1, wherein the upper plate comprises a through hole and the micro-fluid supplying device further comprises a cover layer which overlaps an upper side of the through hole.

9. The micro-fluid supplying device of claim 2, wherein the chamber of the fluid supplier is a bead chamber.

10. The micro-fluid supplying device of claim 1, wherein the intermediate membrane is gas permeable and non-penetrable to liquid.

11. The micro-fluid supplying device of claim 1, wherein the device is configured such that fluid flows through the trap chamber from the fluid supplier to the fluid discharger, and the trap chamber has a width in a direction perpendicular to the fluid flow direction that is smaller than a width of the trap chamber in the direction of fluid flow through the trap chamber.

12. The micro-fluid supplying device of claim 11, further comprising a microchannel connecting the fluid supplier to one end of the trap chamber, and the fluid discharger to the other end of the trap chamber.

13. The micro-fluid supplying device of claim 7, further comprising a pump connected to the pneumatic chamber.

* * * * *